US012046390B2

(12) United States Patent
Okamoto et al.

(10) Patent No.: US 12,046,390 B2
(45) Date of Patent: *Jul. 23, 2024

(54) DOPANT, ELECTROCONDUCTIVE COMPOSITION AND METHOD FOR PRODUCING SAME

(71) Applicants: The University of Tokyo, Tokyo (JP); Daicel Corporation, Osaka (JP)

(72) Inventors: Toshihiro Okamoto, Tokyo (JP); Tadanori Kurosawa, Tokyo (JP); Junichi Takeya, Tokyo (JP); Daiji Ikeda, Tokyo (JP); Yasuyuki Akai, Tokyo (JP)

(73) Assignees: THE UNIVERSITY OF TOKYO, Tokyo (JP); DAICEL CORPORATION, Osaka (JP)

( * ) Notice: Subject to any disclaimer, the term of this patent is extended or adjusted under 35 U.S.C. 154(b) by 156 days.

This patent is subject to a terminal disclaimer.

(21) Appl. No.: 17/634,286

(22) PCT Filed: Aug. 17, 2020

(86) PCT No.: PCT/JP2020/030963
§ 371 (c)(1),
(2) Date: Feb. 10, 2022

(87) PCT Pub. No.: WO2021/039463
PCT Pub. Date: Mar. 4, 2021

(65) Prior Publication Data
US 2022/0336119 A1  Oct. 20, 2022

(30) Foreign Application Priority Data
Aug. 23, 2019  (JP) .................. 2019-153176

(51) Int. Cl.
*H01B 1/00* (2006.01)
*C07C 211/56* (2006.01)
(Continued)

(52) U.S. Cl.
CPC ............ *H01B 1/128* (2013.01); *C07C 211/56* (2013.01); *C07C 311/48* (2013.01); *C07C 2601/16* (2017.05)

(58) Field of Classification Search
CPC .......... H01B 1/00; H01B 1/124; H01B 1/128; C07C 211/56; C07C 311/48
See application file for complete search history.

(56) References Cited

U.S. PATENT DOCUMENTS

| 5,853,906 A | 12/1998 | Hsieh |
| 8,937,300 B2 * | 1/2015 | Wang .................... H05B 33/20 252/301.16 |

(Continued)

FOREIGN PATENT DOCUMENTS

| CN | 104254576 A | 12/2014 |
| JP | 11-193359 A | 7/1999 |

(Continued)

OTHER PUBLICATIONS

English language translation of form PCT/ISA/237 (mailed Oct. 2020).*

(Continued)

*Primary Examiner* — Mark Kopec
(74) *Attorney, Agent, or Firm* — Birch, Stewart, Kolasch & Birch, LLP (57) ABSTRACT

A novel dopant according to the present disclosure includes an anion represented by the following Formula (1) and a counter cation. In Formula (1), $R^1$ and $R^2$ may be each at least one group selected from a nitro group, a cyano group, an acyl group, a carboxyl group, an alkoxycarbonyl group, (Continued)

a haloalkyl group, a sulfo group, an alkylsulfonyl group, an halosulfonyl group, and a haloalkylsulfonyl group, or may be a group formed by $R^1$ and $R^2$ bonded to each other [—$SO_2$-L-$SO_2$—] (where L represents a haloalkylene group). The counter cation may be a radical cation represented by Formula (2), where $R^1$ and $R^2$ represent electron-withdrawing groups that may be bonded to each other to form a heterocycle, and $R^3$ to $R^5$ represent a hydrogen atom, a hydrocarbon group that may have a substituent, or a heterocyclic group that may have a substituent. The dopant is capable of forming an electroconductive composition that shows a high conductivity.

8 Claims, 1 Drawing Sheet

(51) Int. Cl.
*C07C 311/48* (2006.01)
*H01B 1/12* (2006.01)

(56) References Cited

U.S. PATENT DOCUMENTS

| 2013/0092887 | A1 | 4/2013 | Seshadri et al. |
| 2015/0108415 | A1 | 4/2015 | Send et al. |
| 2016/0126020 | A1 | 5/2016 | Snaith et al. |
| 2019/0217648 | A1 | 7/2019 | Katsumoto et al. |
| 2023/0151141 | A1* | 5/2023 | Okamoto ............ C07C 211/56 252/510 |
| 2023/0170107 | A1* | 6/2023 | Okamoto ............ C08L 65/00 252/500 |

FOREIGN PATENT DOCUMENTS

| JP | 2012-253067 A | 12/2012 |
| JP | 2013-87081 A | 5/2013 |
| JP | 2015-151365 A | 8/2015 |
| WO | WO2014/191787 A1 | 12/2014 |
| WO | WO2018/074176 A1 | 4/2018 |

OTHER PUBLICATIONS

English language machine translation of JP 2012-253067 (pub date Dec. 2012).*
English language machine translation of JP 2013-087081 (pub date May 2013).*
Fujimoto et al., "Control of molecular doping in conjugated polymers by thermal annealing", Organic Electronics, 2017, vol. 47, pp. 139-146.
International Search Report, issued in PCT/JP2020/030963, dated Oct. 20, 2020.
Poleschner et al., "$XeF_2$/Fluoride Acceptors as Versatile One-Electron Oxidants", Angewandte Chemie, International Edition, 2013, vol. 52, pp. 12838-12842.
Written Opinion of the International Searching Authority, issued in PCT/JP2020/030963, dated Oct. 20, 2020, (No English language translation).
English translation of the International Preliminary Report on Patentability and Written Opinion of the International Searching Authority for International Application No. PCT/JP2020/030963, dated Mar. 3, 2022.
Chinese Office Action and Search Report for Chinese Application No. 202080059299.1, dated Feb. 28, 2023, with English translation.
Extended European Search Report for European Application No. 20856330.4, dated Jul. 13, 2023.

* cited by examiner

DOPANT, ELECTROCONDUCTIVE COMPOSITION AND METHOD FOR PRODUCING SAME

TECHNICAL FIELD

The present disclosure relates to a novel dopant capable of forming an electroconductive composition that shows a high conductivity (electrical conductivity or electroconductivity), an electroconductive composition including the dopant and an electroconductive organic compound and a method for producing the electroconductive composition, an electronic device including the electroconductive composition, and a novel ionic compound useful as a dopant and a method for producing the ionic composition.

BACKGROUND ART

Organic electronic materials (organic semiconductor materials or electroconductive organic compounds) such as electroconductive polymer compounds (or π-conjugated polymer compounds) are utilized as materials for various electronic devices by taking advantage such as light weight, flexibility, and moldability (or productivity). The organic semiconductor materials are typically subjected to doping (or doped) with dopants to allow high conductivity to be imparted or exhibited. The dopants include a donor (an electron donor or an N-type dopant) that injects electrons as a carrier, and an acceptor (an electron acceptor or a P-type dopant) that withdraws electrons and injects holes. Examples of the donor include alkali metals, alkaline earth metals, quaternary ammoniums, and quaternary phosphoniums, and halogens, Lewis acids, protonic acids, transition metal halides, organic compounds, and the like are known as the acceptor.

Typical acceptors (electron-accepting dopants) include 2,3,5,6-tetrafluoro-7,7,8,8-tetracyanoquinodimethane (F4TCNQ), which is widely utilized in organic semiconductor fields. For example, Non-Patent Literature 1 describes an example in which PBTTT-C16 (poly[2,5-bis (3-hexadecylthiophen-2-yl)thieno[3,2-b]thiophene]) is subjected to molecular implantation doping with F4TCNQ to prepare a P-type organic semiconductor composition.

CITATION LIST

Non-Patent Literature

Non-Patent Literature 1: R. Fujimoto et al. Org. Electron. 47 (2017), 139-146

SUMMARY OF INVENTION

Technical Problem

According to Non-Patent Literature 1, the PBTTT-C16 is oxidized to F4TCNQ as a radical cation to form a hole, whereas the radical anion of the reduced F4TCNQ is stored in the PBTTT-C16, but the F4TCNQ as a radical anion is unstable, and thus not only easily oxidized to the radical cation and then returned to neutrality, but also low in doping efficiency (the proportion of the generated carrier to the doping amount) along with the low oxidizability itself of the F4TCNQ and evaporation (sublimation) of the F4TCNQ due to the effect of heat or the like. At the low doping efficiency, a large amount of dopant is required for increasing the carrier concentration (or conductivity), but if the amount of dopant (impurity) is excessively large, the path (or the electroconductive path) of the charge will be inhibited, thereby causing a decrease in the conductivity, and thus failing to sufficiently improve the conductivity.

In addition, an ordered arrangement of the electroconductive organic compound such as PBTTT-C16 with high crystallinity is important for the improvement of the conductivity, but possibly because the F4TCNQ is stored unstably, there is a possibility that the crystallinity of the PBTTT-C16 after the doping may be decreased, and there is possibility that the crystal structure of the PBTTT-C16 may be disordered in the evaporation of the F4TCNQ. Moreover, the decreased crystallinity makes it difficult to suppress molecular fluctuations and then maintain the aggregate structure (or crystal structure) of the polymer, and there is thus a possibility that the stability (durability under high-temperature environments) may be decreased.

Accordingly, an object of the present disclosure is to provide a novel dopant capable of forming an electroconductive composition that shows a high conductivity, an electroconductive composition including the dopant and a method for producing the electroconductive composition, and an electronic device including the electroconductive composition.

Another object of the present disclosure is to provide a dopant capable of keeping the crystallinity of a doped electroconductive organic compound from being decreased (or maintaining or improving the crystallinity) and forming an electroconductive composition that shows high stability, an electroconductive composition including the dopant and a method for producing the electroconductive composition, and an electronic device including the electroconductive composition.

Still another object of the present disclosure is to provide a dopant that shows a high doping efficiency, an electroconductive composition including the dopant and a method for producing the electroconductive composition, and an electronic device including the electroconductive composition.

Another object of the present disclosure is to provide a novel ionic compound useful as a dopant and a method for producing the ionic compound.

Solution to Problem

The inventors have found, as a result of diligent research for achieving the objectives mentioned above, that the use of, as a dopant, an ionic compound including a nitrogen anion that has a predetermined chemical structure and a counter cation can effectively improve conductivity in an electroconductive composition, thereby achieving the present invention.

More specifically, a novel dopant according to the present disclosure includes an anion represented by Formula (1) below and a counter cation.

[Chem. 1]

(where $R^1$ and $R^2$ each independently represent an electron-withdrawing group, and $R^1$ and $R^2$ may be bonded to each other to form a heterocycle.)

In Formula (1), $R^1$ and $R^2$ may be at least one group selected from a nitro group, a cyano group, an acyl group, a carboxyl group, an alkoxycarbonyl group, a haloalkyl group, a sulfo group, an alkylsulfonyl group, a halosulfonyl group, and a haloalkylsulfonyl group, or may be a sulfonyl-haloalkylene-sulfonyl group formed by $R^1$ and $R^2$ bonded to each other (a haloalkylene-disulfonyl group or a group [—SO$_2$-L-SO$_2$—] (where L represents a haloalkylene group)).

In Formula (1), $R^1$ and $R^2$ may be a fluorosulfonyl group or a fluoroalkylsulfonyl group (for example, a perfluoroalkylsulfonyl group), or may be a sulfonyl-fluoroalkylene-sulfonyl group formed by $R^1$ and $R^2$ bonded to each other (a fluoroalkylene-disulfonyl group or a group [—SO$_2$-L-SO$_2$—] (where L represents a fluoroalkylene group (for example, a perfluoroalkyl group)).

The counter cation may be a radical cation represented by Formula (2) below.

[Chem. 2]

(2)

(where $R^3$ to $R^5$ each independently represent a hydrogen atom, a hydrocarbon group that may have a substituent, or a heterocyclic group that may have a substituent.)

In the Formula (2), $R^3$ to $R^5$ may be an aryl group that may have a substituent, and the substituent may be a group selected from a halogen atom, an alkyl group, a hydroxyl group, an alkoxy group, a nitro group, an amino group, and a substituted amino group.

The present disclosure encompasses an electroconductive composition including the dopant and an electroconductive organic compound. The electroconductive organic compound may be an electroconductive polymer compound having a heterocycle (an electroconductive heteropolymer compound or a heterocyclic electroconductive polymer compound). The electroconductive organic compound may be an electroconductive polymer compound having at least a constituent unit represented by Formula (3) below.

[Chem. 3]

(3)

(where $X^1$ represents an oxygen atom or a sulfur atom, $R^6$ represents a substituent, and n represents an integer from 0 to 2.)

The present disclosure also encompasses a method of producing the electroconductive composition in which the electroconductive organic compound is doped with the dopant and an electronic device including the electroconductive composition.

Furthermore, the present disclosure encompasses an ion pair (or ionic compound) containing an anion represented by Formula (1a) below and a radical cation represented by Formula (2a) below.

[Chem. 4]

(1a)

(where $R^{1a}$ and $R^{2a}$ each independently represent a fluorine atom or a fluoroalkyl group (for example, a perfluoroalkyl group), and $R^{1a}$ and $R^{2a}$ may be bonded to each other to form a fluoroalkylene group (for example, a perfluoroalkylene group).

[Chem. 5]

(2a)

(where $R^{3a}$ to $R^{5a}$ each independently represent a substituent, and m3 to m5 each independently represent an integer from 0 to 5.)

In addition, the present disclosure also encompasses a method of producing the ion pair (or ionic compound) containing an anion represented by Formula (1a) and a radical cation represented by Formula (2a) in which the ionic compound containing the anion represented by Formula (1a) and a monovalent metal ion [in particular, an ionic compound composed of an anion represented by Formula (1a) and a monovalent metal ion] and a neutral compound corresponding to the radical cation represented by Formula (2a) are reacted in the presence of an oxidizing agent.

It is to be noted that, in the present specification and the claims, the term "dopant" refers to an additive (an oxidizing agent (acceptor) or a reducing agent (donor)) for forming organic electronic materials including not only organic semiconductors but also organic thermoelectric materials.

Advantageous Effects of Invention

According to the present disclosure, an ionic compound containing a nitrogen anion that has a predetermined chemical structure is used as a dopant, an electroconductive composition that shows a high conductivity can be thus formed. In addition, the dopant according to the present disclosure is capable of keeping the crystallinity of the electroconductive organic compound from being decreased (or maintaining or improving the crystallinity) even in the case of doping the compound, and forming an electroconductive composition that shows high stability (durability under high-temperature environments). Furthermore, the dopant according to the present disclosure also shows a high doping efficiency, and highly crystalline electroconductive organic compounds that are typically less likely to be doped can be thus also efficiently doped. In addition, the present disclosure can also provide a novel ionic compound useful as a dopant.

DESCRIPTION OF EMBODIMENTS

[Dopant]

A novel dopant (P-type dopant) according to the present disclosure is an ionic compound (also referred to as a salt, an ion pair, an ionic substance, or a heteropolar compound) including an anion represented by Formula (1) and a counter cation (counter cation), and may be a metal complex or a metal compound. In particular, the dopant is preferably composed of an anion represented by Formula (1) and a counter cation. The monovalent anion represented by Formula (1) have a chemical structure delocalized by withdrawal of a negative charge in the nitrogen anion by the two electron-withdrawing groups $R^1$ and $R^2$, and thus even the anion alone has relatively high stability.

When an electroconductive organic compound is doped with the dopant according to the present disclosure as a P-type dopant, the counter cation is converted into a corresponding electrically neutral compound (or atom) and stabilized by the electron received from the electroconductive organic compound. Thus, the anion represented by Formula (1) is released from the ionic bond with the counter cation, and is present with the anion alone stored or embedded in the electroconductive organic compound (for example, in the crystal). Unlike known dopants such as F4TCNQ, even the anion alone represented by Formula (1) as described previously is relatively stable, and can be thus stably present in the composition without donating electrons to the electroconductive organic compound in the radical cationic state. Thus, the doping efficiency is high, and the conductivity can be effectively improved.

In addition, although the reason is not known, the anion represented by Formula (1) is considered stable, and surprisingly, the crystallinity of the electroconductive organic compound can thus be kept from being decreased after the doping (or the crystallinity can be maintained or improved), the conductivity can be further improved, and an electroconductive composition conductive composition that shows high stability can be formed.

It is to be noted that changes (or chemical modifications), such as the types of the electron-withdrawing groups $R^1$ and $R^2$ in Formula (1) and the type of the counter cation, are more easily made to the dopant according to the present disclosure than to known dopants, and the LUMO of the dopant is easily controlled (or tuned) depending on the HOMO of the electroconductive organic compound combined by the doping.

It is to be noted that the anion represented by Formula (1) is considered preferred in terms of the closed shell for a soft base. In the present specification and the claims, the soft acid or base and the hard acid or base mean the definitions (or classification) of the acid and base in the hard and soft acids and bases (HSAB). In addition, for achieving energy gain from coulombic (Coulomb) interaction by efficient charge shielding (for causing the anion represented by Formula (1) and the electroconductive organic compound with holes to be stably present in the electroconductive composition after the doping), it is considered desirable to make pairs of ions that have the same size and shape. Thus, anions that make pairs with the doped electroconductive organic compound (in particular, electroconductive polymer compound) with delocalized holes are preferably large in size.

(Anion Represented by Formula (1))

[Chem. 6]

(1)

(where $R^1$ and $R^2$ each independently represent an electron-withdrawing group, and $R^1$ and $R^2$ may be bonded to each other to form a heterocycle.)

In Formula (1), examples of the electron-withdrawing groups represented by $R^1$ and $R^2$ include a nitro group, a cyano group, an acyl group, a carboxyl group, alkoxycarbonyl groups (e.g., $C_{1-6}$ alkoxy-carbonyl groups such as a methoxycarbonyl group), haloalkyl groups (e.g., perhaloalkyl groups such as a trifluoromethyl group and a trichloromethyl group, sulfo groups, alkylsulfonyl groups (e.g., $C_{1-6}$ alkylsulfonyl groups such as a methylsulfonyl group), halosulfonyl groups, and haloalkylsulfonyl groups.

$R^1$ and $R^2$ may be bonded to each other to form a heterocycle (or a divalent group with $R^1$ and $R^2$ bonded to each other). In the case of forming a heterocycle, the two illustrated electron-withdrawing groups bonded to nitrogen may be bonded directly or bonded (or substituted) with a divalent linking group (such as an alkylene group, a haloalkylene group, an ether group, an ester group, or a combination thereof), and typical examples of the divalent group formed by $R^1$ and $R^2$ bonded to each other include a sulfonyl-haloalkylene-sulfonyl group (a haloalkylene-disulfonyl group or a group [—$SO_2$-L-$SO_2$—] (where L represents a haloalkylene group)).

These electron-withdrawing groups $R^1$ and $R^2$ are preferably a halosulfonyl group or a haloalkylsulfonyl group, or a group with $R^1$ and $R^2$ bonded to each other [—$SO_2$-L-$SO_2$—] (where L represents a haloalkylene group). Examples of the halosulfonyl group include a fluorosulfonyl group and a chlorosulfonyl group. Examples of the haloalkylsulfonyl groups include fluoroalkylsulfonyl groups [e.g., fluoro $C_{1-6}$ alkylsulfonyl groups such as a fluoromethylsulfonyl group, a trifluoroethylsulfonyl group, a trifluoropropylsulfonyl group, a pentafluoropropylsulfonyl group, and perfluoroalkylsulfonyl groups (e.g., perfluoro $C_{1-6}$ alkylsulfonyl groups such as a trifluoromethylsulfonyl group, a pentafluoroethylsulfonyl group, a heptafluoropropylsulfonyl group, and a nonafluorobutylsulfonyl group)]; and chloroalkylsulfonyl groups (e.g., chloro $C_{1-6}$ alkylsulfonyl groups such as a chloromethylsulfonyl group).

Examples of the haloalkylene group represented by L in the group [—$SO_2$-L-$SO_2$—] include fluoroalkylene groups (for example, perfluoroalkylene groups, specifically, perfluoro $C_{2-4}$ alkylene groups such as a tetrafluoroethylene group, a hexafluoropropane-1,3-diyl group, and an octafluorobutane-1,4-diyl group), and chloroalkylene groups (perchloroalkylene groups such as perchloro $C_{2-4}$ alkylene groups).

More preferred examples of $R^1$ and $R^2$ include a fluorosulfonyl group, fluoroalkylsulfonyl groups (such as perfluoroalkylsulfonyl groups), and groups with $R^1$ and $R^2$ bonded to each other [—$SO_2$-L-$SO_2$—] (where L represents a fluoroalkylene group (e.g., a perfluoroalkylene group such as a perfluoro $C_{2-4}$ alkylene group)), even more preferred examples thereof include perfluoroalkylsulfonyl groups such as perfluoro $C_{1-4}$ alkylsulfonyl groups, and among these examples, perfluoro $C_{1-3}$ alkylsulfonyl groups, in particular, perfluoro $C_{1-2}$ alkylsulfonyl groups such as a trifluoromethylsulfonyl group are preferred.

It is to be noted that in the case of forming no heterocycle, the types of the groups $R^1$ and $R^2$ may be different from each other, but typically, are preferably identical.

Typical examples of the anion represented by Formula (1) include anions represented by Formula (1a) below.

[Chem. 7]

(1a)

(where $R^{1a}$ and $R^{2a}$ each independently represent a fluorine atom or a fluoroalkyl group, and $R^{1a}$ and $R^{2a}$ may be bonded to each other to form a fluoroalkylene group.)

In Formula (1a), examples of the fluoroalkyl group represented by $R^{1a}$ and $R^{2a}$ include fluoroalkyl groups [e.g., fluoro $C_{1-6}$ alkyl groups such as a fluoromethyl group, a trifluoroethyl group, a trifluoropropyl group, a pentafluoropropyl group, and perfluoroalkyl groups (for example, perfluoro $C_{1-6}$ alkyl groups such as a trifluoromethyl group, a pentafluoroethyl group, a heptafluoropropyl group, and a nonafluorobutyl group)], and chloroalkyl groups (for example, chloro $C_{1-6}$ alkyl groups such as a chloromethyl group).

$R^{1a}$ and $R^{2a}$ may be bonded to each other to form a heterocycle (or $R^{1a}$ and $R^{2a}$ may bond to each other to form a fluoroalkylene group). Examples of such a fluoroalkylene group include fluoro $C_{2-4}$ alkylene groups such as perfluoroalkylene groups (for example, perfluoro $C_{2-4}$ alkylene groups such as a tetrafluoroethylene group, a hexafluoropropane-1,3-diyl group, and an octafluorobutane-1,4-diyl group).

Preferred examples of the group $R^{1a}$ and $R^{2a}$ include a fluorine atom, perfluoroalkyl groups (such as perfluoro $C_{1-4}$ alkyl groups), and perfluoroalkylene groups with $R^{1a}$ and $R^{2a}$ bonded to each other (such as a perfluoro $C_{2-4}$ alkylene group), more preferred examples thereof include perfluoroalkyl groups such as perfluoro $C_{1-3}$ alkyl groups, and in particular, perfluoro $C_{1-2}$ alkyl groups such as a trifluoromethyl group are preferred.

It is to be noted that in the case of forming no cycle, the types of the groups $R^{1a}$ and $R^{2a}$ may be different from each other, but typically, are preferably identical.

Specific examples of the anion represented by Formula (1) or (1a) include a bis(fluorosulfonyl)imide anion where $R^{1a}$ and $R^{2a}$ are a fluorine atom [i.e. an anion represented by the formula [($FSO_2$)$_2$N$^-$ (also referred to as FSI$^-$ or FSA$^-$)]; anions where $R^{1a}$ and $R^{2a}$ are perfluoroalkyl groups (such as perfluoro $C_{1-4}$ alkyl groups), more specifically, a bis(trifluoromethanesulfonyl)imide anion [i.e., an anion represented by the formula [($CF_3SO_2$)$_2$N$^-$] or the formula [$Tf_2$N$^-$] (also referred to as TFSI$^-$ or TFSA$^-$)], an N-trifluoromethanesulfonyl-N-nonafluorobutanesulfonylimide anion [i.e. an anion represented by the formula [$CF_3SO_2$—N$^-$—$SO_2C_4F_9$], and a bis(nonafluorobutansulfonyl)imide anion [i.e. an anion represented by the formula [($C_4F_9SO_2$)$_2$N$^-$]; and a cyclic anion that is a perfluoroalkylene group where $R^{1a}$ and $R^{2a}$ are bonded to each other (such as a perfluoro $C_{2-4}$ alkylene group), more specifically, a hexafluoropropane-1,3-di(sulfonyl)imide anion [i.e., an anion where a divalent group with $R^{1a}$ and $R^{2a}$ bonded to each other is a hexafluoropropane-1,3-diyl group in Formula (1a)]. Among these examples, anions where $R^{1a}$ and $R^{2a}$ are a fluorine atom or perfluoroalkyl groups (such as perfluoro $C_{1-4}$ alkyl groups) are preferred, anions where $R^{1a}$ and $R^{2a}$ are perfluoro $C_{1-3}$ alkyl groups are further preferred, and in particular, anions where $R^{1a}$ and $R^{2a}$ are perfluoro $C_{1-2}$ alkyl groups are preferred, such as TFSI$^-$.

(Counter Cation)

The counter cation may be a divalent or higher-valent (polyvalent) cation, but is typically a monovalent cation. In addition, in response to the fact that the anion represented by Formula (1) is a soft base, the counter cation is preferably a soft acid. Furthermore, the counter cation may be a non-radical cation, but is preferably a radical cation. Radical cations make it easy to accept electrons from the electro-conductive organic compound with high oxidizability (to inject holes) at the time of doping, thereby allowing the doping efficiency to be effectively improved, and often allowing the counter cation to be stably present in the composition after accepting electrons to be neutral. Examples of such a counter cation include radical cations represented by Formula (2) below.

[Chem. 8]

(2)

(where $R^3$ to $R^5$ each independently represent a hydrogen atom, a hydrocarbon group that may have a substituent, or a heterocyclic group that may have a substituent.)

Examples of the hydrocarbon groups represented by $R^3$ to $R^5$ in Formula (2) include an alkyl group, a cycloalkyl group, an aryl group, and aralkyl group. Examples of the alkyl group include linear or branched $C_{1-6}$ alkyl groups, such as a methyl group, an ethyl group, a n-butyl group, and a t-butyl group. Examples of the cycloalkyl groups include $C_{3-10}$ cycloalkyl groups, such as a cyclopentyl group and a cyclohexyl group. Examples of the aryl group include $C_{6-14}$ aryl groups such as a phenyl group, a 1-naphthyl group, and a 2-naphthyl group, and bi $C_{6-10}$ aryl groups such as a biphenylyl group. Examples of the aralkyl group include $C_{6-14}$ aryl-$C_{1-6}$ alkyl groups, such as a benzyl group and a phenethyl group. Among these hydrocarbon groups, the alkyl groups and the aryl groups are preferred, and the aryl groups are further preferred.

The heterocyclic groups represented by $R^3$ to $R^5$ may be aromatic or non-aromatic, and examples thereof include heterocyclic groups containing at least one heteroatom selected from a nitrogen atom, an oxygen atom, and a sulfur atom. In addition, the heterocyclic groups may be monocyclic heterocyclic groups, or may be polycyclic heterocyclic groups that have a monocyclic heterocycle and one or more heterocycles and/or hydrocarbon rings (aromatic hydrocarbon rings or non-aromatic hydrocarbon rings) fused (e.g., ortho-fused or ortho- and peri-fused). The ring that forms the heterocyclic groups (each ring that is fused with each other in the case of a polycyclic heterocyclic group) are often 5- to 7-membered rings, preferably 5- or 6-membered rings.

Typical examples of heterocyclic groups include heterocyclic groups containing a nitrogen atom as a heteroatom [for example, 5- or 6-membered monocyclic heterocyclic groups containing a nitrogen atom, such as a pyrrolyl group, an imidazolyl group, a pyridyl group, and a pyrazinyl group; and polycyclic heterocyclic groups having a 5- or 6-membered ring containing a nitrogen atom, such as an indolyl group, a quinolyl group, an isoquinolyl group, a quinazolyl group, a carbazolyl group, a carbolinyl group, a phenanthridinyl group, an acridinyl group, a phenazinyl group, and a naphthyridinyl group]; heterocyclic groups containing an oxygen atom as a heteroatom [for example, 5- or 6-membered monocyclic heterocyclic groups containing an oxygen atom, such as a furyl group; and polycyclic heterocyclic groups having a 5- or 6-membered ring containing an oxygen atom, such as a chromenyl group]; heterocyclic groups containing a sulfur atom as a heteroatom [for example, 5- or 6-membered monocyclic heterocyclic groups containing a sulfur atom, such as a thienyl group; and polycyclic heterocyclic groups having a 5- or 6-membered ring containing a sulfur atom, such as a benzothienyl group, a thianthrenyl group, and a thienothienyl group]; and heterocyclic groups containing different heteroatoms [for example, 5- or 6-membered monocyclic heterocyclic groups containing different heteroatoms, such as a morpholinyl group, an isothiazolyl group, and an isoxazolyl group; and polycyclic heterocyclic groups having a 5- or 6-membered ring containing different heteroatoms, such as a phenoxathiinyl group.

The hydrocarbon groups or heterocyclic groups represented by $R^3$ to $R^5$ may each be aromatic. The hydrocarbon groups or heterocyclic groups represented by $R^3$ to $R^5$ may have one or more substituents. Examples of the substituents include halogen atoms (e.g., a fluorine atom, a chlorine atom, a bromine atom, and an iodine atom), alkyl groups (e.g., linear or branched $C_{1-6}$ alkyl groups such as a methyl group, an ethyl group, a n-butyl group, and a t-butyl group), a hydroxyl group, an alkoxy group (e.g., linear or branched $C_{1-6}$ alkoxy groups such as a methoxy group and a t-butoxy group), acyl groups (e.g., $C_{1-8}$ alkylcarbonyl groups such as a formyl group and an acetyl group, $C_{6-12}$ aryl-carbonyl groups such as a benzoyl group), alkoxycarbonyl groups (e.g., $C_{1-6}$ alkoxy-carbonyl groups such as a methoxycarbonyl group and an ethoxycarbonyl group), a cyano group, a nitro group, amino groups, and substituted amino groups (e.g., mono or dialkylamino groups such as dimethylamino groups, mono or diacylamino groups such as acetylamino groups). These substituents may be used alone, or two or more thereof may be used in combination. Among these substituents, the halogen atoms, the alkyl groups, the alkoxy groups, and the like are often used, and the halogen atoms (in particular, a bromine atom) are preferred.

In addition, the number of substitutions with the substituents can be selected depending on the types of the hydrocarbon groups or heterocyclic groups substituted, for example, and may be selected from an integer range, for example, approximately from 0 to 6 (for example, from 0 to 5), preferably from 0 to 4 (for example, from 0 to 3), even more preferably approximately from 1 to 2 (in particular, 1). It is to be noted that the substitution positions may be any position, but, for example, in the case where a phenyl group as a hydrocarbon group is substituted with the substituent, the substitution at least at the p-position is preferred.

Preferred examples of $R^3$ to $R^5$ include hydrocarbon groups that may have a substituent, and more preferred examples thereof include aryl groups that may have a substituent (e.g., $C_{6-14}$ aryl groups that may have a substituent, such as a phenyl group, a naphthyl group, and a biphenyl group), and even more preferred examples thereof include $C_{6-12}$ aryl groups that may have a substituent, in particular, $C_{6-10}$ aryl groups that may have a substituent, and particularly preferred is a phenyl group. For $R^3$ to $R^5$, hydrocarbon groups (in particular, aryl groups such as a phenyl group) preferably have at least the substituent. It is to be noted that preferred substituents, preferred numbers of substitutions, and substitution positions for the hydrocarbon groups (in particular, aryl groups such as a phenyl group) are the same as those according to the preferred embodiment.

Specific examples of $R^3$ to $R^5$ include haloaryl groups (e.g., mono- to tri-halo $C_{6-10}$ aryl groups such as a p-chlorophenyl group, a p-bromophenyl group, and a p-iodophenyl group), alkylaryl groups (e.g., mono- to tri-$C_{1-4}$ alkyl $C_{6-10}$ aryl groups such as a p-methylphenyl group and a dimethylphenyl group), and alkoxyaryl groups (for example, mono- to tri-$C_{1-4}$ alkoxy $C_{6-10}$ aryl groups such as a p-methoxyphenyl group). Among these examples, preferred are the haloaryl groups (such as mono- or di-halo $C_{6-10}$ aryl groups), and more preferred are the monohaloaryl groups (in particular, p-halophenyl groups such as a p-bromophenyl group).

It is to be noted that $R^3$ to $R^5$ may be identical to or different from each other, but typically, are preferably identical to each other.

Typical examples of the radical cations represented by Formula (2) include trialkylaminium radical cations, tricycloalkylaminium radical cations, triarylaminium radical cations, and triaralkylaminium radical cations, and in particular, a radical cation represented by Formula (2a) below is preferred.

[Chem. 9]

(2a)

(where $R^{3a}$ to $R^{5a}$ each independently represent a substituent, and m3 to m5 each independently represent an integer from 0 to 5.)

In Formula (2a), the substituents represented by $R^{3a}$ to $R^{5a}$ are the same as the groups illustrated as substituents that the hydrocarbon groups or heterocyclic groups represented by $R^3$ to $R^5$ of Formula (2) may have, including preferred aspects.

The numbers of substitutions represented by m3 to m5 may be, for example, an integer approximately from 0 to 4 (for example, from 0 to 3), preferably from 1 to 2 (in particular, 1), and is typically 1 or more. It is to be noted that the numbers of substitutions m3 to m5 may be different from each other, but typically, are preferably equal to each other.

In the case where m3 to m5 are 1 or more, the types of substituents $R^{3a}$ to $R^{5a}$ that are substituted for different phenyl groups may be different from each other, but typically, are preferably identical to each other. In addition, in the case where m3 to m5 are two or more, the types of two or more substituents $R^{3a}$ to $R^{5a}$ that are substituted for the same phenyl group may be identical to each other or different from each other.

In the case where m3 to m5 are 1 or greater, the substitution positions of the corresponding substituents $R^{3a}$ to $R^{5a}$ may be any position, but the substitution at least at the p-position with respect to the phenyl group is preferred.

Specific examples of the radical cations represented by Formula (2) or (2a) include radical cations of corresponding neutral compounds (amine compounds) such as: triphenylamine; tris(halophenyl)amines [for example, tris(mono or dihalophenyl)amines such as a tris(p-chlorophenyl) amine, a tris(p-bromophenyl)amine, a tris(p-iodophenyl) amine, a tris(m-bromophenyl)amine, and a tris(o-bromophenyl)amine]; tris(alkylphenyl)amines [for example, tris (mono- or di-$C_{1-4}$alkyl-phenyl)amines, such as a tris(p-methylphenyl)amine and a tris(p-t-butylphenyl)amine]; and tris(alkoxyphenyl)amines [for example, tris(mono- or di-$C_{1-4}$alkoxy-phenyl)amines, such as a tris(p-methoxyphenyl) amine and a tris(p-t-butoxyphenyl)amine. Among these examples, the tris(halophenyl)amines such as tris(monohalophenyl)amines are preferred, and more preferably, the tris(p-halophenyl)amines such as tris(p-bromophenyl)amine may be employed.

The dopant according to the present disclosure has only to include an anion represented by Formula (1) and the counter cation, and the anion represented by Formula (1) [or Formula (1a)] and the counter cation (for example, a radical cation represented by Formula (2) or Formula (2a)) may be each included alone or as combination of two or more types. Typically, the dopant is often composed of only the anion represented by Formula (1) and the counter cation (in particular, only the anion represented by Formula (1) [or Formula (1a)] and the single counter cation].

Typical examples of the dopant according to the present disclosure include an ionic compound composed of a combination of an anion represented by Formula (1a) and a radical cation represented by Formula (2a) as a counter cation. It is to be noted that such an ionic compound obtained by combining an anion represented by Formula (1a) and a radical cation represented by Formula (2a) is a novel substance.

Specific example thereof include an ionic compound obtained by combining: an anion selected from an anion that is a group where $R^{1a}$ and $R^{2a}$ are a fluorine atom or a perfluoroalkyl group (such as a perfluoro $C_{1-6}$ alkyl group) in Formula (1a) and a cyclic anion that is a perfluoroalkylene group (such as a perfluoro $C_{2-4}$ alkylene group) where $R^{1a}$ and $R^{2a}$ are bonded to each other [for example, the anions specifically illustrated as the anion represented by Formula (1) or (1a), such as FSI⁻, TFSI⁻, and a hexafluoropropane-1,3-di(sulfonyl)imide anion]; and a radical cation represented by Formula (2a) [for example, a radical cation, corresponding to an amine compound selected from triphenylamine, tris(halophenyl)amines, tris(alkylphenyl)amines, and tris(alkoxyphenyl)amines, specifically illustrated as the radical cation represented by Formula (2) or (2a)]. Among these examples, an ionic compound obtained by combining an anion where $R^{1a}$ and $R^{2a}$ are perfluoroalkyl groups (such as perfluoro $C_{1-4}$ alkyl groups) and a radical cation of a tris(halophenyl)amine [for example, a tris(monohalophenyl)amine], and more preferably, an ionic compound obtained by combining a TFSI⁻ and a tris(p-halophenyl) amine such as tris(p-bromophenyl)amine may be employed.

(Producing Method)

The method for producing the dopant (or ionic compound) according to the present disclosure is not particularly limited, and may be manufactured by, for example, a method of reacting, in the presence of an oxidizing agent, an ionic compound containing an anion represented by Formula (1) [in particular, Formula (1a)] and a monovalent metal ion, and a neutral compound corresponding to a predetermined counter cation, specifically, a neutral compound (or a corresponding amine compound) corresponding to a radical cation represented by Formula (2) [in particular, Formula (2a)].

The monovalent metal ion may be, for example, an alkali metal ion or the like, and typical examples thereof include transition metal ions, for example, ions of metal elements in Group 11 of the periodic table, such as Cu⁺, Ag⁺, and Au⁺. These monovalent metal ions may be used alone, or two or more thereof may be used in combination. A preferred monovalent metal ion may be Ag⁺.

The ionic compound containing an anion represented by Formula (1) [in particular, Formula (1a)] and a monovalent metal ion has only to contain an anion represented by Formula (1) [in particular, Formula (1a)] and a monovalent metal ion, and the anion represented by Formula (1) [or Formula (1a)] and the monovalent metal ion may be each included alone or as a combination of two or more types. Typically, the compound is often composed of only the anion represented by Formula (1) and the monovalent metal ion (in particular, a single anion represented by Formula (1) [or Formula (1a)] and a single monovalent metal ion).

Examples of the ionic compound containing an anion represented by Formula (1) [in particular, Formula (1a)] and a monovalent metal ion include monovalent metal salts of the anions specifically exemplified as the anion represented by Formula (1) or (1a), and for example, a monovalent metal salt of TFSI⁻, such as bis(trifluoromethanesulfonyl)imide silver (AgTFSI). The ionic compounds containing an anion represented by Formula (1) [in particular, Formula (1a)] and a monovalent metal ion can be used alone, or two or more thereof can be used in combination.

The neutral compound (or corresponding amine compound) corresponding to the radical cation represented by Formula (2) [in particular, Formula (2a)] include amine compounds corresponding to the radical cations specifically illustrated as the radical cation represented by Formula (2) or (2a), such as tris(halophenyl)amines [for example, a tris(p-bromophenyl)amine].

The proportion of the ionic compound containing an anion represented by Formula (1) [in particular, Formula (Ta)] and a monovalent metal ion may be for example, approximately from 1 to 5 mol (for example, from 1.1 to 3 mol), preferably approximately from 1.2 to 2 mol (for example, from 1.3 to 1.5 mol), with respect to 1 mol of the neutral compound corresponding to the radical cation represented by Formula (2) [in particular, Formula (2a)].

The oxidizing agent may be any oxidizing agent that is capable of oxidizing the neutral compound by one electron to form the radical cation represented by Formula (2) [in particular, Formula (2a)], and examples thereof include simple halogens (such as chlorine $Cl_2$, bromine $Br_2$, iodine $I_2$), and halogen acids [for example, hypohalite salts (for example, alkali metal salts of hypohalous acids, such as sodium hypochlorite NaClO), halite salts (for example, alkali metal salts of halous acids, such as sodium chlorite $NaClO_2$), halogen acid salts (for example, alkali metal salts of halogen acids, such as potassium bromate $KBrO_3$), and perhalides (for example, alkali metal perhalide salts, such as potassium metaperiodate KIO$_4$)]. These oxidizing agents can be used alone, or two or more thereof can be used in combination. Among these oxidizing agents, the simple halogens (in particular, iodine I$_2$) is preferred.

The proportion of the oxidizing agent may be for example, approximately from 1 to 5 mol (for example, from 1 to 3 mol), preferably approximately from 1 to 2 mol (for example, from 1 to 1.5 mol), more preferably 1 mol with respect to 1 mol of the neutral compound corresponding to the radical cation represented by Formula (2) [in particular, Formula (2a)].

The reaction may typically be carried out in the presence of a solvent. Examples of the solvent include solvents that are inert to the reaction, such as aprotic solvents, for example, ethers (for example, chain ethers such as diethyl ether, and cyclic ethers such as tetrahydrofuran and dioxane). Typically, chain ethers such as diethyl ether are often used.

The reaction may typically be carried out in an inert gas atmosphere (such as a nitrogen gas or a noble gas), and may be performed while stirring. The reaction temperature may be, for example, approximately from −70° C. to +60° C. (for example, from −50° C. to +40° C.), preferably from −40° C. to +30° C. The reaction time may be, for example, approximately from 1 minute to 1 hour (for example, from 5 minutes to 30 minutes), preferably from 10 minutes to 20 minutes. After completion of the reaction, separation and refinement may be carried out by known separation and purification means such as filtration, drying, extraction, recrystallization, re-precipitation, and combinations thereof.

[Electroconductive Composition]

The electroconductive composition according to the present disclosure includes the dopant according to the present disclosure and an electroconductive organic compound (or an organic semiconductor compound). The electroconductive composition may include another dopant (second dopant) that is different from the dopant (first dopant) according to the present disclosure, but typically, preferably includes substantially no second dopant (such as a known dopant such as F4TCNQ). It is to be noted that the first dopant may be used alone or as a combination of two or more types, and is typically used alone.

(Electroconductive Organic Compound)

The electroconductive organic compound may be an electroconductive low-molecular-weight compound or may be an electroconductive polymer compound. It is to be noted that, in the present specification and the claims, the "electroconductive organic compound" ("electroconductive low-molecular-weight compound" and "electroconductive polymer compound") means a compound that exhibits a property as a semiconductor or a conductor (or a good conductor) with the compound doped with the dopant according to the present disclosure [or a substance that has a conductivity (electrical conductivity or electroconductivity) of, for example, 10$^{-10}$ S/cm or more], and the electroconductive organic compound is used in the sense of also including a compound that exhibits a property as an insulator with the compound alone including no dopant (pre-doped or undoped) [for example, a substance that has a conductivity of less than 10$^{-10}$ S/cm].

Typical examples of the electroconductive low-molecular-weight compound include acenes (for example, naphthacene, chrysene, pyrene, pentacene, picene, perylene, hexadecene, heptacene, dibenzopentacene, coronene, tetrabenzopentacene, and ovalene); phthalocyanines (for example, phthalocyanine (such as a copper phthalocyanine), naphthalocyanine, and subphthalocyanine); carbazoles [for example, 1,3,5-tris[2,7-(N,N-(p-methoxyphenyl)amino)-9H-carbazole-9-yl]benzene (SGT405)]; thiophenes [for example, 2,5-bis[4-(N,N-bis(p-methoxyphenyl)amino)phenyl]-3,4-ethylenedioxythiophene (H101), and 2,3,4,5-tetrakis[4-(N,N-bis(p-methoxyphenyl)amino)phenyl]thiophene (H111)]; tetracarboxylic diimides [for example, 1,4,5,8-naphthalenetetracarboxylic diimide, 2,3,6,7-naphthalenetetracarboxylic diimide, and 2,3,6,7-anthracenetetracarboxylic diimide]; and triptycenes [for example, 2,6,14-tris[5'-(4-(N, N-bis(p-methoxyphenyl)amino)phenyl)-thiophene-2'-yl]trypticene (T103)].

Typical examples of the electroconductive polymer compound (or conjugated polymer compound) include aliphatic conjugated polymer compounds (for example, polyacetylenes such as trans-polyacetylene, and polyphenylacetylenes); aromatic conjugated polymer compounds [for example, poly(p-phenylene), poly(m-phenylene), and polyfluorene]; heterocyclic conjugated polymer compounds [for example, polypyrroles (for example, poly(pyrrole-2,5-diyl)), and polythiophenes [for example, polythiophene, poly alkylthiophene, poly[5,5'-bis(3-alkyl-2-thienyl)-2,2'-bithiophene] (or PQT), poly[2,5-bis(3-alkylthiophene-2-yl) thieno[3,2-b]thiophene] (or PBTTT), and poly(3,4-ethylenedioxythiophene) (or PEDOT)]]; heteroatom-containing conjugated polymer compounds [for example, polyaniline, polyazobenzene, and polytriarylamines (for example, poly [bis(4-phenyl)-(2,4,6-trimethylphenyl)-amine] (or PTAA)]; ladder-shaped (or double-chain) conjugated polymer compounds [for example, polyacene, and polyphenanthrene]; and mixed conjugated polymer compounds [for example, poly(p-phenylenevinylene), and poly(p-phenylene sulfide)].

These electroconductive organic compounds may be prepared from commercially available products or by known methods. In addition, these electroconductive organic compounds may be used alone, or two or more thereof may be used in combination. Among these compounds, the electroconductive polymer compounds are preferred from the perspective of excellent formation ability (productivity) and heat resistance in the preparation of electronic devices and the like. The electroconductive polymer compounds may be used alone, or two or more thereof may be used in combination, and typically the electroconductive polymer compounds are often used alone. The electroconductive organic compound (or electroconductive polymer compound) in the electroconductive composition according to the present disclosure is typically capable of forming a P-type organic semiconductor, and among the electroconductive polymer compounds mentioned above, the electroconductive polymer compounds having at least a heterocycle are preferred, such as heterocyclic conjugated polymer compounds.

The electroconductive polymer compounds having a heterocycle may be conjugated polymer compounds including at least a constituent unit having a heterocycle in the molecular structures (in particular, in the main chains). The heterocycle may be a monocyclic heterocycle, or may be a polycyclic heterocycle that has a monocyclic heterocycle and one or more rings [heterocycle and/or hydrocarbon rings (aromatic hydrocarbon rings or non-aromatic hydrocarbon rings)] fused (e.g., ortho-fused or ortho- and peri-fused). The ring that forms the heterocycle (each ring that is fused with each other in the case of a polycyclic heterocycle) is often a 5- to 7-membered ring, preferably a 5- or 6-membered ring.

Examples of the heteroatom that forms the heterocycle include a nitrogen atom, an oxygen atom, and a sulfur atom. These heteroatoms may be included alone in the heterocycle, or two or more thereof may be included therein in combination. Among these heteroatoms, the nitrogen atom and the sulfur atom are preferred, and the sulfur atom is more preferred. The heterocycle may be a heterocycle containing an oxygen atom, such as a furan ring, a heterocycle containing a nitrogen atom, such as a pyrrole ring, or the like, but is preferably a heterocycle containing at least a sulfur atom as a heteroatom, such as a thiophene ring, a benzothiophene ring, a thienothiophene ring, a benzothiadiazole ring [in particular, a heterocycle having (including or internally having) a thiophene ring structure such as a thiophene ring, a benzothiophene ring, or a thienothiophene ring].

Typical examples of the constituent unit having such a heterocycle include constituent units represented by Formula (3) below.

[Chem. 10]

(3)

(where $X^1$ represents an oxygen atom or a sulfur atom, $R^6$ represents a substituent, and n represents an integer from 0 to 2.)

In Formula (3), preferred $X^1$ is a sulfur atom.

Examples of the substituent represented by $R^6$ include alkyl groups (for example, linear or branched $C_{1-20}$ alkyl groups such as a hexyl group, an octyl group, a 2-ethylhexyl group, a dodecyl group, a tetradecyl group, a hexadecyl group, and an octadecyl group), and alkoxy groups (for example, linear or branched $C_{1-20}$ alkoxy groups such as a hexyloxy group, an octyloxy group, a 2-ethylhexyloxy group, a dodecyloxy group, a tetradodecyloxy group, a hexadecyloxy group, and an octadecyloxy group). Among these substituents, the alkyl groups are preferred, such as linear or branched $C_{6-18}$ alkyl groups.

The number of substituents n is often 0 or 1, and preferably 1 from the perspective of solubility. It is to be noted that in the case where n is 2, the types of the two groups $R^6$ may be identical to or different from each other.

Specific examples of the constituent units (or divalent groups) represented by Formula (3) include thiophene-2,5-diyl groups, and 3-alkylthiophene-2,5-diyl groups (for example, 3-$C_{6-18}$-alkylthiophene-2,5-diyl groups such as 3-hexylthiophene-2,5-diyl groups). These constituent units represented by Formula 3 may be used alone, or two or more thereof may be combined.

The electroconductive polymer compound having a heterocycle preferably includes at least the constituent unit represented by Formula (3), and further preferably includes a constituent unit represented by the following Formula (3A) from the perspective of high crystallinity and easy improvement in conductivity. Typically, the high crystallinity of the electroconductive organic compound makes it difficult to achieve doping (makes the doping efficiency likely to be decreased), thus making it difficult to improve the conductivity, but the dopant according to the present disclosure is also excellent in doping efficiency for highly crystalline electroconductive organic compounds, thus allowing the conductivity to be effectively improved.

[Chem. 11]

(3A)

(where $X^{1a}$ and $X^{1b}$ represent an oxygen atom or a sulfur atom, $R^{6a}$ and $R^{6b}$ represent a substituent, n1 and n2 represent an integer from 0 to 2, $X^{2a}$ and $X^{2b}$ represent an oxygen atom or a sulfur atom, and $R^{7a}$ and $R^{7b}$ represent a hydrogen atom or a substituent.)

In Formula (3A), preferred $X^{1a}$ and $X^{1b}$ are a sulfur atom. The types of $X^{1a}$ and $X^{1b}$ may be different from each other, but typically, are often identical to each other.

Examples of the substituents represented by $R^{6a}$ and $R^{6b}$ include the same groups as those of $R^6$ in Formula (3), including preferred aspects thereof. The numbers of substitutions n1 and n2 are often 0 or 1, and preferably 1 from the perspective of solubility. The n1 and n2 may be different from each other, but typically, are often equal to each other. In the case where n1 and n2 is 1, the substitution positions of $R^{6a}$ and $R^{6b}$ may be each either the 3- or 4-position of a 5-membered heterocycle containing $X^{1a}$ and $X^{1b}$, but are typically the 3-position of the 5-membered heterocycle (closer to the fused heterocycle containing central $X^{2a}$ and $X^{2b}$).

It is to be noted that in the case where n1 and n2 are from 1 to 2, the types of the $R^{6a}$ and $R^{6b}$ may be different from each other, but typically, are often identical to each other. In addition, in the case where n1 and n2 are 2, the types of the two groups $R^{6a}$ and two groups $R^{6b}$ may be identical to or different from each other.

Preferred $X^{2a}$ and $X^{2b}$ are a sulfur atom. The types of $X^{2a}$ and $X^{2b}$ may be different from each other, but typically, are often identical to each other.

Examples of the substituents represented by $R^{7a}$ and $R^{7b}$ include the same groups as those of $R^6$ in Formula (3), including preferred aspects thereof. Preferred $R^{7a}$ and $R^{7b}$ are a hydrogen atom.

Typical examples of the constituent unit (or divalent group) represented by Formula (3A) include constituent units represented by the following Formula (3a) (such as a constituent unit having 2,5-bis(3-alkylthiophene-2-yl)thieno[3,2-b]thiophene).

[Chem. 12]

(3a)

(where $R^{6a}$ and $R^{6b}$ are the same as those of Formula (3A), including preferred aspects thereof.)

Specific examples of the constituent units represented by Formula (3a) include constituent units having 2,5-bis(3-C$_{6-20}$alkylthiophene-2-yl)thieno[3,2-b]thiophene ($R^{6a}$ and $R^{6b}$ are C$_{6-20}$ alkyl groups), such as a constituent unit where $R^{6a}$ and $R^{6b}$ are dodecyl groups, a constituent unit where $R^{6a}$ and $R^{6b}$ are tetradecyl groups, a constituent unit where $R^{6a}$ and $R^{6b}$ are hexadecyl groups, and a constituent unit where $R^{6a}$ and $R^{6b}$ are octadecyl groups. The constituent units represented by Formula (3A), (3a), or the like may be used alone, or two or more thereof may be combined.

It is to be noted that in the electroconductive polymer compound having a heterocycle, the proportion of the constituent unit having a heterocycle [preferably a heterocycle containing at least a sulfur atom as a heteroatom, in particular, a heterocycle having a thiophene ring structure (such as a constituent unit represented by Formula (3)) may be, for example, approximately 10 mol % or greater (for example, 30 mol % or greater), preferably 50 mol % or greater (for example, 70 mol % or greater), more preferably 90 mol % or greater (for example, substantially 100 mol %), based on all of the constituent units.

In addition, the proportion of the constituent unit (or divalent group) represented by Formula (3) may be, for example, approximately from 10 to 100 mol % (for example, from 30 to 90 mol %), preferably approximately from 50 to 80 mol % (for example, from 60 to 70 mol %), based on all of the constituent units. The proportion of the constituent unit represented by Formula (3A) [in particular, (3a)] may be, for example, approximately 10 mol % or greater (for example, 30 mol % or greater), preferably 50 mol % or greater (for example, 70 mol % or greater), more preferably 90 mol % or greater (for example, substantially 100 mol %), based on all of the constituent units.

Typical examples of the electroconductive polymer compound having a heterocycle include the heterocyclic conjugated polymer compounds mentioned above, and among the example, polythiophenes such as a polythiophene, a polyalkylthiophene, a PQT, a PBTTT, and a PEDOT are preferred.

Examples of the polythiophene include poly(thiophene-2,5-diyl). Examples of the polyalkylthiophene include poly (3-C$_{1-18}$ alkylthiophene-2,5-diyl) such as poly(3-methylthiophene-2,5-diyl), poly(3-hexylthiophene-2,5-diyl) (or P3HT), poly(3-octylthiophene-2,5-diyl) (or P3OT), and poly(3-dodecylthiophene-2,5-diyl) (or P3DDT). Examples of the PQT include poly[5,5'-bis(3-C$_{1-18}$ alkyl-2-thienyl)-2,2'-bithiophene] such as poly[5,5'-bis(3-dodecyl-2-thienyl)-2,2'-bithiophene] (or PQT-C12). Examples of the PBTTT include poly[2,5-bis(3-C$_{1-18}$ alkylthiophene-2-yl)thieno[3,2-b]thiophene] such as poly[2,5-bis(3-dodecylthiophen-2-yl)thieno[3,2-b]thiophene] (or PBTTT-C12), poly [2,5-bis (3-tetradecylthiophene-2-yl)thieno[3,2-b]thiophene] (or PBTTT-C14), and poly[2,5-bis(3-hexyldecylthiophene-2-yl)thieno[3,2-b]thiophene] (or PBTTT-C16).

The electroconductive polymer compound having a heterocycle (in particular, polythiophenes) may be used alone, or two or more thereof may be combined. Among these compounds, the polythiophene, the polyalkylthiophene, the PQT, the PBTTT, and the like are preferred, and the PBTTT is even more preferred.

The molecular weight of the electroconductive polymer compound is not particularly limited, and, for example, in the case of measurement by gel permeation chromatography (GPC), the number average molecular weight Mn in terms of polystyrene may be approximately from 500 to 5000000 (for example, from 5000 to 100000), preferably from 10000 to 50000 (for example, from 15000 to 40000), more preferably from 20000 to 30000 (for example, from 23000 to 27000), the molecular weight distribution or PDI (Mw/Mn) may be, for example, approximately from 1 to 20 (for example, from 1.1 to 10), preferably from 1.2 to 5 (for example, from 1.3 to 3), more preferably from 1.5 to 2.5 (for example, from 1.6 to 2). The excessively large Mn has the possibility of decreasing the solubility and the like, thereby decreasing the formation ability, whereas the excessively small Mn has the possibility of decreasing the heat resistance, mechanical properties, and the like.

In the electroconductive composition, the proportion of the total amount of the dopant and electroconductive organic compound according to the present disclosure may be, for example, approximately 50 mass % or greater (for example, 80 mass % or greater), preferably 90 mass % or greater (substantially 100 mass %). The excessively low proportion of the dopant has the possibility of failing to improve the carrier density, thereby failing to sufficiently improve the conductivity, whereas the excessively high proportion thereof has the possibility of decreasing the crystallinity of the electroconductive organic compound, thereby decreasing the conductivity. The dopant according to the present disclosure is high in doping efficiency, and thus capable of effectively improving the carrier density and the conductivity even in small amounts.

The electroconductive composition may include known additives and the like without impairing the advantageous effects of the present disclosure. Examples of the additives include leveling agents, and adhesion promoters (such as silane coupling agents). These additives can be used alone or two or more types can be used in combination. The proportion of the additives may be, for example, approximately 30 parts by mass or less (for example, 10 parts by mass or less), preferably 5 parts by mass or less (for example, from 0 to 1 parts by mass) with respect to 100 parts by mass in total of the dopant and electroconductive organic compound.

In addition, there is no need for the electroconductive composition to include any solvent, but the electroconductive composition may include a solvent, if necessary, for forming a thin membrane, a film, or the like of an organic semiconductor by a simple method such as printing or application (coating).

Examples of the solvent include aromatic hydrocarbons (for example, benzene, toluene, xylene, and anisole); halogenated hydrocarbons (for example, halo C$_{1-6}$ alkanes such as dichloromethane, chloroform, and 1,2-dichloroethane, chlorobenzene, and dichlorobenzene); alcohols (for example, C$_{1-6}$ alkanemonools such as methanol, ethanol, 2-propanol, n-butanol, and t-butanol; and C$_{2-4}$ alkanediols such as an ethylene glycol); ethers (chain ethers such as a diethyl ether and a diisopropyl ether, and cyclic ethers such as tetrahydrofuran and dioxane); glycol ethers [for example, cellosolves (such as a methyl cellosolve), carbitols (such as a methyl carbitol), (poly) C$_{2-4}$ alkylene glycol mono C$_{1-4}$ alkyl ethers such as a triethylene glycol monomethyl ether and propylene glycol monomethyl ether; and (poly) C$_{2-4}$ alkylene glycol di C$_{1-4}$ alkyl ethers such as ethylene glycol dimethyl ether and dipropylene glycol dimethyl ether]; glycol ether acetates [for example, cellosolve acetates (for example, C$_{1-4}$ alkyl cellosolve acetates such as a methyl cellosolve acetate), carbitol acetates (for example, C$_{1-4}$ alkyl carbitol acetates such as a methyl carbitol acetate), and (poly) C$_{2-4}$ alkylene glycol mono C$_{1-4}$ alkyl ether acetates such as propylene glycol monomethyl ether acetate and dipropylene glycol monobutyl ether acetate]; ketones (e.g., chain ketones such as acetone and methyl ethyl ketone, and cyclic ketones such as cyclohexanone); esters (e.g., acetic acid esters such as an ethyl acetate, and lactic acid esters such as a methyl lactate); carbonates (e.g., chain carbonates such as dimethyl carbonate, and cyclic carbonates such as an ethylene carbonate and propylene carbonate); nitriles (such as acetonitrile, propionitrile, and benzonitrile); amides (such as N,N-dimethylformamide, N,N-dimethylacetamide, and N-methyl-2-pyrrolidone); sulfoxides (such as dimethylsulfoxide); and mixed solvents thereof. Typically, the aromatic hydrocarbons, the halogenated hydrocarbons (for example, o-dichlorobenzene), and the like are often utilized.

In the case where the electroconductive composition includes a solvent, the respective components and the solvent may be mixed and then optionally filtered to prepare the composition. The solid content concentration in the electroconductive composition (solution or dispersion) can be selected depending on the applying method or the like, and may be, for example, approximately from 0.001 to 20 mass % (for example, from 0.01 to 10 mass %), preferably from 0.1 to 5 mass % (for example, from 0.5 to 3 mass %), particularly from 0.6 to 2 mass % (for example, from 0.7 to 1.3 mass %).

(Method for Producing Electroconductive Composition

The method for producing an electroconductive composition including the dopant and electroconductive organic compound according to the present disclosure includes at least a doping of doping the electroconductive organic compound with the dopant. There is not necessarily any need to form the electroconductive organic compound to be subjected to the doping, into a predetermined shape, and the compound may be formed into a predetermined shape after the doping or in the doping, but is typically formed into a predetermined shape (for example, a membrane, a film, or the like) before the doping.

For the method of forming into a predetermined shape, known forming methods can be used, and in the case of formation into a shape such as a membrane or a film, the shape may be formed by a dry process such as a vacuum deposition method or a sputtering method, or may be formed by a wet process (such as coating). The wet process is preferred from the perspective of formation ability (or productivity).

In accordance with the wet process, a composition (solution or dispersion) including at least the electroconductive organic compound and the solvent is subjected to printing or application (or coating) onto at least one surface of a base material (or a substrate), and the solvent is removed from the obtained coating film to obtain a film.

The base material (or substrate) is not particularly limited, and may be, for example, a glass plate, a silicon wafer, a plastic film (for example, a transparent resin film such as a polyethylene terephthalate film), or the like. These base materials may have, if necessary, one or more functional layers (for example, a conductive layer such as an ITO, an insulating layer such as $SiO_2$, or a self-assembled monolayer (SAM) such as β-phenethyltrimethoxysilane β-PTS)) formed on the surfaces of the base materials.

The printing or applying method is not particularly limited, and may be any known method such as an air knife coating method, a roll coating method, a gravure coating method, a blade coating method, a bar coating method, a die coating method, a dip coating method, a spray coating method, a spin coating method, a casting method, an edge casting method, a drop casting method, a screen printing method, an ink-jet printing method, and a compression orientation method. Typically, the spin coating method, the edge casting method, the drop casting method, the ink-jet printing method, and the like are often utilized, and the spin coating method and the like are preferred from the perspective of ease of film formation (or productivity).

The solvent is removed from the obtained coating film by a known method such as natural drying, drying under heating and/or under reduced pressure, or spin drying (or spin drying), thereby allowing the formation of a thin membrane or film. These drying methods may be used alone, or two or more thereof may be combined. The heating temperature in the case of drying under heating may be, for example, approximately from 30 to 100° C., preferably from 40 to 80° C.

The obtained thin membrane or film may be subjected to an annealing treatment. The annealing treatment temperature can be selected from the range, for example, approximately from 50 to 400° C. (for example, from 80 to 380° C.), and may be, for example, approximately from 100 to 360° C. (for example, from 150 to 350° C.), preferably from 200 to 340° C. (for example, from 250 to 330° C.), more preferably from 280° C. to 320° C. The annealing treatment time may be, for example, approximately from 10 minutes to 12 hours, preferably from 30 minutes to 8 hours, more preferably from 1 to 6 hours (for example, from 2 to 4 hours). It is to be noted that the annealing treatment may be carried out under an air atmosphere, or may be carried out under an inert gas atmosphere such as a nitrogen gas or a noble gas (helium, argon, or the like), and is preferably carried out under an inert gas (in particular, argon) atmosphere.

In addition, the doping method is not particularly limited, and known methods can be used, which include a gas-phase doping method, a liquid-phase doping method of impregnating a dopant solution with the electroconductive organic compound (such as a membrane or film of the electroconductive organic compound), an electrochemical doping method of immersing and then electrolyzing the electroconductive organic compound in an electrolyte solution containing a dopant, an ion implantation method, and an induced doping method.

Among these methods, the liquid-phase doping method is often utilized. The solvent for preparing the dopant solution for use in the liquid-phase doping method is not particularly limited as long as the solvent is capable of dissolving or dispersing the dopant, and examples thereof include the solvents illustrated in the section of the electroconductive composition, and typically, polar solvents of nitriles (such as an acetonitrile) are often used. The concentration of the dopant solution may be selected from the range of, for example, approximately from 0.01 to 100 mmol/L (for example, from 0.1 to 10 mmol/L), and may be, for example, approximately from 0.3 to 5 mmol/L (for example, from 0.5 to 2 mmol/L), preferably from 0.5 to 1.5 mmol/L (for example, from 0.8 to 1.2 mmol/L). It is to be noted that for efficient doping (for biasing the balance), the used amount of dopant in the dopant solution is, typically, often excessively large with respect to the electroconductive organic compound (or the repeating unit of the electroconductive polymer compound).

The impregnation (or immersion) of the electroconductive organic compound (such as a membrane or film of the electroconductive organic compound) with or in the dopant solution may be carried out under heating, if necessary. The heating temperature may be lower than or equal to the boiling point of the dopant solution, and may be, for example, approximately from 20 to 60° C. (for example, from 30 to 50° C.), preferably from 35 to 45° C. The impregnation time may be, for example, approximately from 1 minute to 12 hours (for example, from 5 to 30 minutes), preferably from 10 to 20 minutes.

After impregnating the dopant solution with the electroconductive organic compound, the obtained electroconductive composition may be dried by any known method to remove the solvent, and for example, in the case where the electroconductive organic compound is a membrane or a film, drying by heating is often carried out after spin drying. The number of revolutions in the spin drying may be, for example, approximately from 500 to 5000 rpm (for example, from 1000 to 2000 rpm), and the time may be approximately from 1 second to 1 hour (from 5 to 60 seconds, for example). In addition, the temperature in the drying by heating may be, for example, approximately from 40 to 300° C. (for example, from 60 to 100° C.), and the time may be, for example, approximately from 1 minute to 12 hours (for example, from 5 to 30 minutes).

It is to be noted that in the case where the electroconductive composition includes the above-mentioned additives or the like, these additives may be mixed with the electroconductive organic compound before or after the doping or during the doping.

The thickness (average thickness) of the thin membrane or film obtained in this manner may be appropriately selected depending on the use application, and may be, for example, approximately from 1 to 5000 nm, preferably from 30 to 1000 nm, more preferably from 50 to 500 nm.

(Electroconductive Composition Properties and Electronic Device)

The electroconductive composition according to the present disclosure exhibit a high conductivity, which may be, for example, approximately from 10 to 10000 S/cm (for example, from 100 to 5000 S/cm), preferably from 300 to 3000 S/cm (for example, from 500 to 2500 S/cm), more preferably from 1000 to 2000 S/cm (for example, from 1200 to 1800 S/cm). It is to be noted that in the present specification and the claims, the conductivity can be measured by the method described in the examples described later.

The electroconductive composition according to the present disclosure may typically be a P-type semiconductor, and because of the high conductivity as described above, can be utilized as a material for forming electronic devices, for example, semiconductor elements such as switching elements, rectifying elements (diodes), and transistors, photoelectric conversion elements (such as solar cell elements and organic electroluminescence (EL) elements), and thermoelectric conversion elements.

Each aspect disclosed in the present specification can be combined with any other feature disclosed herein.

EXAMPLES

Hereinafter, the present disclosure is described in greater detail based on examples, but the present disclosure is not limited to these examples.

[Synthesis of Ionic Compound]

Example 1

[Chem. 13]

Bis(trifluoromethanesulfonyl)imide silver [also referred to as AgTFSI, 1.36 g, 3.51 mmol], tris(4-bromophenyl)amine (1.21 g, 2.51 mmol), and diethyl ether ($Et_2O$, 100 mL) were mixed, stirred for 20 minutes, and then cooled to −36° C. Into the mixture, a mixed liquid of iodine ($I_2$, 0.64 g, 2.51 mmol)/$Et_2O$ (30 mL) was delivered by drops over 15 minutes, and the mixture was then increased to room temperature. The precipitate was collected by filtration and dried under reduced pressure for 1 hour at room temperature to obtain a crude product (1.77 g, yield: 93%) of a dark purple solid. The obtained crude product was dissolved in a dry methylene chloride ($CH_2Cl_2$, 90 mL) and then filtered, and the obtained filtrate was poured into dry $Et_2O$ (360 mL) at −26° C. Thereafter, the temperature was increased to room temperature, the precipitate was filtered again, then collected, and dried under reduced pressure for 2 hours at room temperature to obtain a target product of a dark purple solid (an ionic compound (also referred to as TPA-TFSI) of an anion represented by Formula (1a-1) and a cation represented by Formula (2a-1), 1.41 g, and yield: 74%). The results of elemental analysis are shown below.

Anal. Calcd for $C_{20}H_{12}Br_3F_6N_2O_4S_2$: C, 31.52; H, 1.59; N, 3.68. Found: C, 31.55; H, 1.80; N, 3.80.

[Measurement of Ultraviolet-Visible-Near Infrared (UV-Vis-NIR) Spectrum]

Example 2

Prepared by the method described below was a measurement sample (electroconductive composition) obtained by liquid-phase doping a polymer compound having a repeating unit represented by the following Formula (3a-1) ("PBTTT-C14" from Aldrich, Mn=25 300, PDI=1.8) with the ionic compound (TPA-TFSI) obtained according to Example 1.

[Chem. 14]

(3a-1)

(where R represents an n-tetradecyl group (group-$C_{14}H_{29}$.)

More specifically, a 1 mass % ortho-dichlorobenzene solution of PBTTT-C14 was applied by spin coating (500 rpm for 5 seconds, and then 2000 rpm for 60 seconds) onto a glass substrate to prepare a spin coating film from 40 to 100 nm in average thickness. The obtained spin coating film was immersed in a dopant solution with a concentration of 1 mmol/L (an acetonitrile solution of the ionic compound obtained according to Example 1) for 15 minutes at a temperature of 40° C. After the immersion, the film was subjected to spin drying (1500 rpm, 30 seconds) and then dried for 10 minutes at a temperature of 80° C. to prepare the measurement sample (electroconductive composition).

Figure 1:
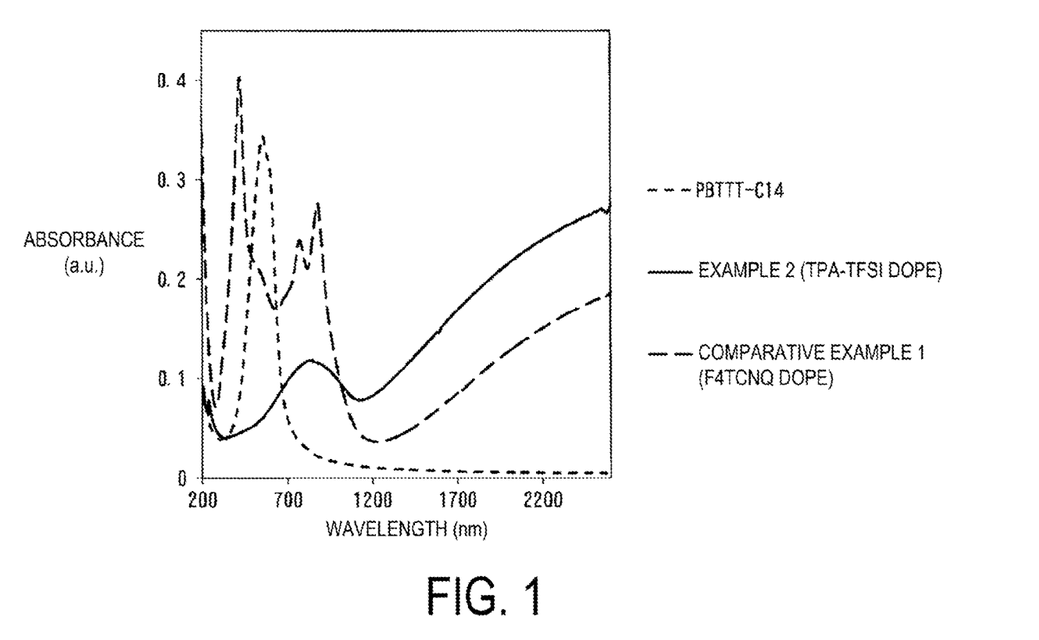
FIG. 1 shows ultraviolet-visible near-infrared (UV-Vis-NIR) absorption spectra of electroconductive compositions obtained according to Example 2 and Comparative Example 1, and PBTTT-C14 not doped with a dopant.

The obtained measurement sample was subjected to a measurement at an interval of 1 nm in the range from 200 to 2700 nm with the use of an ultraviolet-visible near-infrared spectrophotometer (from JASCO) to measure an ultraviolet-visible-near-infrared (UV-Vis-NIR) absorption spectrum. The measurement result is illustrated in FIG. 1. It is to be noted that, for reference, FIG. 1 illustrates a spectrum of only the PBTTT-C14 doped with no dopant as a measurement sample.

Comparative Example 1

In the same manner as in Example 2 with the exception of using 2,3,5,6-tetrafluoro-7,7,8,8-tetracyanoquinone dimethane (F4-TCNQ) instead of the ionic compound obtained according to Example 1, an ultraviolet-visible-near-infrared (UV-Vis-NIR) absorption spectra was measured. The measurement result is illustrated in FIG. 1.

As is clear from FIG. 1, Example 2 has, as compared with Comparative Example 1 doped with F4-TCNQ, a greatly decreased peak near 500 nm derived from the neutral PBTTT-C14, and greatly increased absorption around 1200 to 2500 nm derived from PBTTT-C14 radical cations. Thus, Example 2 was higher in doping efficiency than in the case of doping with the F4-TCNQ according to Comparative Example 1. It is to be noted that the sharp absorption around 400 nm in Comparative Example 1 is believed to indicate absorption by the neutral F4-TCNQ, whereas the doublet absorption around 700 to 1000 nm is believed to indicate absorption by the F4-TCNQ anion.

[Measurement of X-Ray Rocking Curve]

Example 3

Figure 2:
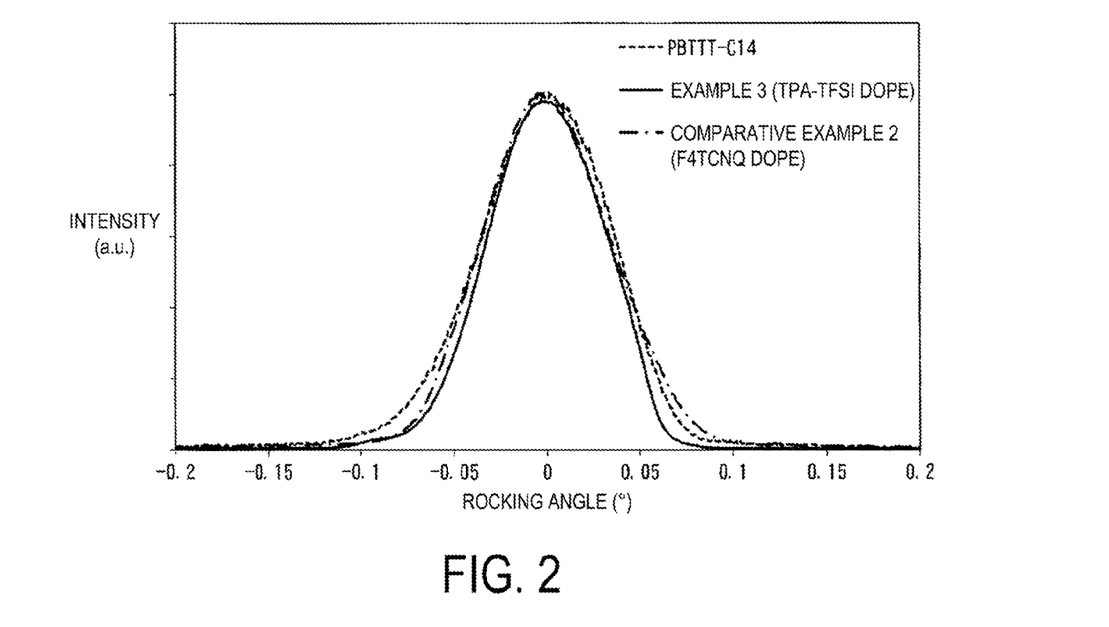
FIG. 2 shows the measurement results of X-ray rocking curves of electroconductive compositions obtained according to Example 3 and Comparative Example 2, and PBTTT-C14 not doped with a dopant.

For a measurement sample (electroconductive composition) prepared in the same manner as in Example 2, an X-ray rocking curve was measured with the use of CuKα as an X-ray source by using an X-ray diffractometer ("SmartLab" from Rigaku). The measurement results are illustrated in FIG. 2. It is to be noted that, for reference, FIG. 2 also illustrates a measurement result in the case of only the PBTTT-C14 doped with no dopant as a sample.

Comparative Example 2

In the same manner as in Example 3 with the exception of using 2,3,5,6-tetrafluoro-7,7,8,8-tetracyanoquinone dimethane (F4TCNQ) instead of the ionic compound obtained according to Example 1, an X-ray rocking curve was measured. The measurement results are illustrated in FIG. 2.

As is clear from FIG. 2, it has been determined that Example 3 has a full width at half maximum (FWHM) decreased and has a high crystallinity after the doping, as compared with Comparative Example 2 doped with the F4TCNQ. Particularly, as compared with the case of the PBTTT-C14 alone, the full width at half maximum was decreased by about 2% in Comparative Example 2, whereas the full width at half maximum was decreased by about 10% in Example 3. From this result, it is believed that the TFSI anion after the doping made a great contribution to improved crystallinity.

[Measurement of Conductivity]

Example 4

In the same manner as in Example 2 with the exception of using a glass substrate with a gold electrode for four-terminal measurement instead of the glass substrate, a measurement sample was prepared by forming a film of PBTTT-C14 and liquid-phase doping with a dopant solution containing the ionic compound according to Example 1.

When the conductivity of the obtained measurement sample was measured under the measurement condition of current input: 1 µA with the use of a digital multimeter ("Keiythley 2000 digital multimeter" from Keiythley), and the digital multimeter indicated a conductivity that was as high as 1500 S/cm.

Comparative Example 3

When the conductivity was measured in the same manner as in Example 4 with the exception of using 2,3,5,6-tetrafluoro-7,7,8,8-tetracyanoquinone dimethane (F4-TCNQ) instead of the ionic compound obtained according to Example 1, the conductivity was 250 S/cm.

INDUSTRIAL APPLICABILITY

The dopant according to the present disclosure is capable of effectively improving the conductivity in the electroconductive composition, and the electroconductive composition including the dopant according to the present disclosure can be thus effectively utilized as various electronic devices, for example, organic semiconductor devices such as rectifying elements (diodes), switching elements or transistors (organic thin film transistors) [for example, junction transistors (bipolar transistors), and field-effect transistors (unipolar transistors)], photoelectric conversion elements (such as solar cell elements and organic EL elements), and thermoelectric conversion elements.

The invention claimed is:

1. An electroconductive composition comprising a dopant and an electroconductive organic compound,
wherein the dopant comprises:
an anion represented by Formula (1):

(1)

where $R^1$ and $R^2$ each independently represent an electron-withdrawing group, and $R^1$ and $R^2$ may be bonded to each other to form a heterocycle; and
a counter cation,
wherein the electroconductive organic compound is an electroconductive polymer compound comprising a constituent unit represented by Formula (3A);

(3A)

where $X^{1a}$ and $X^{1b}$ represent an oxygen atom or sulfur atom $R^{6a}$ and $R^{6b}$ represent a substituent, n1 and n2 represent an integer from 0 to 2, $X^{2a}$ and $X^{2b}$ represent an oxygen atom of sulfur atom, and $R^{7a}$ and $R^{7b}$ represent a hydrogen atom or a substituent.

2. The electroconductive composition according to claim 1, wherein in Formula (1), $R^1$ and $R^2$ are each at least one group selected from a nitro group, a cyano group, an acyl group, a carboxyl group, an alkoxycarbonyl group, a haloalkyl group, a sulfo group, an alkylsulfonyl group, a halosulfonyl group, and a haloalkylsulfonyl group, or a group formed by $R^1$ and $R^2$ bonded to each other [—$SO_2$-L-$SO_2$—] where L represents a haloalkylene group.

3. The electroconductive composition according to claim 1, wherein in Formula (1), $R^1$ and $R^2$ are each a fluorosulfonyl group or a fluoroalkylsulfonyl group, or a group formed by $R^1$ and $R^2$ bonded to each other [—$SO_2$-L-$SO_2$—] where L represents a fluoroalkylene group.

4. The electroconductive composition according to claim 1, wherein the counter cation is a radical cation represented by Formula (2):

(2)

where $R^3$ to $R^5$ each independently represent a hydrogen atom, a hydrocarbon group that may have a substituent, or a heterocyclic group that may have a substituent.

5. The electroconductive composition according to claim 4, wherein in Formula (2), $R^3$ to $R^5$ are each an aryl group that may have a substituent, and the substituent is a group selected from a halogen atom, an alkyl group, a hydroxyl group, an alkoxy group, a nitro group, an amino group, and a substituted amino group.

6. A method for producing the electroconductive composition described in claim 1, wherein the electroconductive organic compound is doped with the dopant.

7. An electronic device comprising the electroconductive composition described in claim 1.

8. The electroconductive composition according to claim 1, wherein in Formula (3A), $R^{6a}$ and $R^{6b}$ represent an alkyl group or an alkoxy group, $R^{7a}$ and $R^{7b}$ represent an alkyl group or an alkoxy group, and
a proportion of the constituent unit represented by Formula (3A) is 100 mol % based on all of the constituent units.

* * * * *